United States Patent
Tam

(10) Patent No.: US 11,311,595 B2
(45) Date of Patent: Apr. 26, 2022

(54) CLEAR SKIN SUPPLEMENT AND MEDICINAL COMPOSITION FOR ACNE

(71) Applicant: VT CM Pty Ltd, Ashwood (AU)

(72) Inventor: Vivian Tam, Ashwood (AU)

(73) Assignee: VC TM PTY LTD

( * ) Notice: Subject to any disclaimer, the term of this patent is extended or adjusted under 35 U.S.C. 154(b) by 140 days.

(21) Appl. No.: 16/956,460

(22) PCT Filed: Dec. 20, 2018

(86) PCT No.: PCT/AU2018/000266
§ 371 (c)(1),
(2) Date: Jun. 19, 2020

(87) PCT Pub. No.: WO2019/119018
PCT Pub. Date: Jun. 27, 2019

(65) Prior Publication Data
US 2020/0323941 A1    Oct. 15, 2020

(30) Foreign Application Priority Data
Dec. 20, 2017   (AU) ................................ 2017905083

(51) Int. Cl.
| | | |
|---|---|---|
| *A61K 36/756* | (2006.01) | |
| *A61K 9/00* | (2006.01) | |
| *A61K 9/20* | (2006.01) | |
| *A61K 36/288* | (2006.01) | |
| *A61K 36/355* | (2006.01) | |
| *A61K 36/484* | (2006.01) | |
| *A61K 36/515* | (2006.01) | |
| *A61K 36/534* | (2006.01) | |
| *A61K 36/537* | (2006.01) | |
| *A61K 36/65* | (2006.01) | |
| *A61K 36/73* | (2006.01) | |
| *A61K 36/744* | (2006.01) | |
| *A61K 36/86* | (2006.01) | |
| *A61K 36/9068* | (2006.01) | |

(52) U.S. Cl.
CPC .......... *A61K 36/756* (2013.01); *A61K 9/0053* (2013.01); *A61K 9/2095* (2013.01); *A61K 36/288* (2013.01); *A61K 36/355* (2013.01); *A61K 36/484* (2013.01); *A61K 36/515* (2013.01); *A61K 36/534* (2013.01); *A61K 36/537* (2013.01); *A61K 36/65* (2013.01); *A61K 36/73* (2013.01); *A61K 36/744* (2013.01); *A61K 36/86* (2013.01); *A61K 36/9068* (2013.01)

(58) Field of Classification Search
CPC .. A61K 36/756; A61K 9/0053; A61K 9/2095; A61K 36/288; A61K 36/355; A61K 36/484; A61K 36/515; A61K 36/534; A61K 36/537; A61K 36/65; A61K 36/73; A61K 36/744; A61K 36/86; A61K 36/9068
See application file for complete search history.

(56) References Cited

FOREIGN PATENT DOCUMENTS

| | | |
|---|---|---|
| CN | 101214321 A | 7/2008 |
| CN | 102210837 A | 10/2011 |
| CN | 104784573 A | 7/2015 |
| WO | 2019119018 A1 | 6/2019 |

OTHER PUBLICATIONS

"ARTG Entry for product 281059—Zilch", Australian Government—Department of Health, Therapeutic Goods Administration, ARTG start date (considered publication date) Oct. 6, 2016; Retrieved online at http://search.tga.gov.au/s/search.html?collection=tga-artg &profile=record&meta_i=281059.
"Guidelines for safe Chinese herbal medicine practice", Chinese Medicine Board of Australia: Chinese herbal Medicine Guidelines, Nov. 2015.
International Application Serial No. PCT/AU2018/00026, Search Report and Written Opinion dated Feb. 12, 2019, 8 pgs.

*Primary Examiner* — Aaron J Kosar
(74) *Attorney, Agent, or Firm* — Kwan & Olynick LLP

(57) ABSTRACT

There is disclosed a clear skin supplement/medicinal component for acne comprising: an orally administered dosage comprising of between about 3000-9000 mg of the Chinese medicinal composition comprising by ratio: around 3.8-7.6% of each of *Prunus persica, Carthamus tinctorius, Angelica dahurica, Gleditsia sinensis, Viola yedoensis, Paeonia suffruticosa* and *gardenia jasminoides*; around 5.7-7.6% of each of *Oldenlandia diffusa* and *Scutellaria baicalensis*; around 3.8-5.7% of *Salvia miltiorrhiza*; around 2.5-5.7% of *Phellodendron amurense*; around 2.5-7.6% of *Gentiana scabra*; and around 0-7.6% of each of *Taraxacum mongolicum* and any one of *Lonicera japonica/Rhizoma Coptidas/Sophora flavescens*.

4 Claims, No Drawings

CLEAR SKIN SUPPLEMENT AND MEDICINAL COMPOSITION FOR ACNE

CROSS-REFERENCE TO RELATED APPLICATIONS

The present application is the U.S. national phase of PCT Application No. PCT/AU2018/000266 filed Dec. 20, 2018, which invention claims priority from Australian provisional patent application no. 2017905083, filed Dec. 20, 2017, the entire contents of both applications are incorporated herein by reference.

TECHNICAL FIELD OF INVENTION

The present disclosure relates generally to a dietary supplement and medicinal composition for enhancing skin health in relation to skin conditions such as acne and skin inflammation using naturally occurring ingredients as part of an oral treatment process, and a process for preparing such a supplement application.

BACKGROUND

In Western civilization, the treatment of conditions, such as acne and other skin related conditions has largely focused upon cleansing the skin and applying pharmaceutical treatments such as a topical creams and gels that concentrate on unblocking clogged pores. Failure of such treatments has often resulted in combining such a topical treatment with an oral antibiotic that acts to kill the bacteria that causes inflammation around the blocked pores.

Typically such treatments have been moderately successful in treating minor skin inflammation and conditions associated with teenagers who may be experiencing skin problems due to changing hormone levels and increased oil production. However, there may be side effects with such treatments and such a two-step treatment may not be successful for all sufferers. Thus, for those suffering from a more severe case of acne or skin inflammation, there may be much frustration in finding a successful treatment method, which could incorporate laser or light treatment to reduce inflammation and attack the acne-causing bacteria. Such treatments may be time consuming and expensive, whilst having varying degrees of success.

In Eastern civilizations, there has been a historical approach to addressing various health conditions through the use of natural occurring products and invigorants. Traditional Chinese medicinal materials including natural animals and plants, have long been used in the form of supplements to address various conditions, including skin conditions, with ongoing success. However, the manner in which such raw materials are processed and prepared for use has long prevented the take-up of such treatments by Western civilizations. Therefore, there is a need to provide a traditional Chinese supplement composition with a simple formula and a convenient process for preparing the composition for use.

The above references to and descriptions of prior proposals or products are not intended to be, and are not to be construed as, statements or admissions of common general knowledge in the art. In particular, the following prior art discussion does not relate to what is commonly or well known by the person skilled in the art, but assists in the understanding of the inventive step of the present invention of which the identification of pertinent prior art proposals is but one part.

SUMMARY

According to a first aspect, there is provided a clear skin supplement for consumption by an individual afflicted with a skin condition comprising of between about 3000-9000 mg of the Chinese medicinal composition comprising by ratio: around 3.8-7.6% of each of *Prunus persica, Carthamus tinctorius, Angelica dahurica, Gleditsia sinensis, Viola yedoensis, Paeonia suffruticosa* and *gardenia jasminoides*; around 5.7-7.6% of each of *Oldenlandia diffusa* and *Scutellaria baicalensis*; around 3.8-5.7% of *Salvia miltiorrhiza*; around 2.5-5.7% of *Phellodendron amurense*; around 2.5-7.6% of *Gentiana scabra*; and around 0-7.6% of each of *Taraxacum mongolicum* and any one of *Lonicera japonica/Rhizoma Coptidas/Sophora flavescens*.

In an embodiment of the first aspect, the supplement also comprises by ratio between 0-3.8% of each of *Zingiber officinale* and *Glycyrrhiza uralensis*; and 0-5.7% of *Angelica polymorpha*.

According to another aspect, there is provided a clear skin supplement comprising by ratio: around 3.8-7.6% of each of *Prunus persica, Carthamus tinctorius, Angelica dahurica, Gleditsia sinensis, Viola yedoensis, Paeonia suffruticosa* and *gardenia jasminoides*; around 5.7-7.6% of each of *Oldenlandia diffusa* and *Scutellaria baicalensis*; around 3.8-5.7% of *Salvia miltiorrhiza*; around 2.5-5.7% of *Phellodendron amurense*; around 2.5-7.6% of *Gentiana scabra*; and around 0-7.6% of each of *Taraxacum mongolicum* and *Lonicera japonica*.

According to yet another aspect, there is provided a method of treating skin inflammation conditions comprising: oral administering a daily dosage of a clear skin supplement to a patient suffering from a skin inflammation, wherein said daily dosage is administered in a tablet of about 750 mg of the supplement, the tablet comprising: 2-3% of each of *Prunus persica, Carthamus tinctorius, Salvia miltiorrhiza, Paeonia suffruticosa, Gentiana scabra* and *Scutellaria baicalensis;* 4-5% of each of, *Oldenlandia diffusa, Herba, Angelica dahurica, Gleditsia sinensis, Spina, Viola yedoensis, Herba, Taraxacum mongolicum, Herba, Lonicera japonica;* 2.3-3.5% of *Phellodendron amurense;* and 1.5-2.5% of *gardenia jasminoides*, by weight.

In an embodiment of this aspect, the supplement composition may also comprises 0-2% each of *Zingiber officinale, Angelica polymorpha* and *Glycyrrhiza uralensis* by weight.

In accordance with another aspect, there is disclosed a supplement composition of approximately comprising: 2-3% of each of *Prunus persica, Carthamus tinctorius, Salvia miltiorrhiza, Paeonia suffruticosa, Gentiana scabra* and *Scutellaria baicalensis;* 4-5% of each of, *Oldenlandia diffusa, Herba, Angelica dahurica, Gleditsia sinensis, Spina, Viola yedoensis, Herba, Taraxacum mongolicum, Herba, Lonicera japonica;* 2.3-3.5% of *Phellodendron amurense;* and 1.5-2.5% of *gardenia jasminoides*, by weight.

DETAILED DESCRIPTION

The present disclosure will be described below in further detail with reference to various examples.

In some examples, the clear skin supplement is provided in tablet or capsule form for oral ingestion by an individual having a skin inflammation condition, such as acne. The tablet may be uncoated however in some instances, a coating, such as an enteric coating, may be applied to the tablet for controlling the delivery and ingestion of the active ingredients contained therein. However, in alternative embodiments, the present disclosure may present the ingredients in a powdered or raw form whereby they may be ingested orally or applied topically to the surface of the skin experiencing inflammation, to address such inflammation.

The primary ingredients of the present disclosure are listed below in Table 1, together with the part of the plant that the ingredient is taken from.

Each of the above ingredients have various properties in accordance with Chinese medicine, to deal with a variety of conditions associated with the skin. For example, *Prunus Persica, Carthamus tinctorius* and *Salvia miltiorrhiza* have been known to increase blood circulation and to treat blood stagnation. *Hedyotis diffusa* is also known as being useful in reducing heat and toxicity levels and breaking down blood stagnation, as have *Viola* Yedoensis, *Taraxacum Mongolicum, Lonicera Japonica, Phellodendron Amurense, Paeonia Suffruticosa* and *Gardenia* Florida. *Angelica Dahurica* and *Gleditsia Sinensis* are also known in their use of reducing swellings and abscesses on the skin.

*Zingiber officinale, Angelica polymorpha,* and *Glycyrrhiza uralensis* are each secondary ingredient and are known for their ability to work with other ingredients to enhance their efficacy.

TABLE 1

In relation to *Lonicera Japonica*, this ingredient may be replaced with more readily available ingredients such as *Rhizoma Coptidis* or *Sophora Flavescens*, depending upon availability.
In this embodiment, potato starch is used as an excipient or carrier to bind the ingredients together in tablet form.

| AHN | Plant Part |
|---|---|
| *Primus persica* | Kernel |
| *Carthamus tinctorius* | Flower |
| *Salvia miltiorrhiza* | Root |
| *Hedyotis diffusa*, Herba | Plant |
| *Angelica dahurica* | Root |
| *Gleditsia sinensis*, Spina | Spine |
| *Viola yedoensis*, Herba | Plant |
| *Taraxacum mongolicum*, Herba | Plant |
| *Lonicera japonica* | Flower |
| *Phellodendron amurense* | Bark |
| *Paeonia suffruticosa* | Root Bark |
| *gardenia florida* | Fruit |
| *Gentiana scabra* | Root |
| *Scutellaria baicalensis* | Root |
| *Zingiber officinale* | Rhizome |
| *Angelica polymorpha* | Root |
| *Glycyrrhiza uralensis* | Root |
| Starch-Potato | |

Table 2 depicts the proportions of each ingredient per 750 mg tablet.

TABLE 2

| AHN | Type | % per 750 mg Tablet |
|---|---|---|
| *Prunus persica* | Active/primary | 2-3 |
| *Carthamus tinctorius* | Active/primary | 2-3 |
| *Salvia miltiorrhiza* | Active/primary | 2-3 |
| *Oldenlandia diffusa*, Herba | Active/primary | 4-5 |
| *Angelica dahurica* | Active/primary | 4-5 |
| *Gleditsia sinensis*, Spina | Active/primary | 4-5 |
| *Viola yedoensis*, Herba | Active/primary | 4-5 |
| *Taraxacum mongolicum*, Herba | Active/primary | 4-5 |
| *Lonicera japonica* | Active/secondary | 4-5 |
| *Phellodendron amurense* | Active/primary | 2.5-3.5 |
| *Paeonia suffruticosa* | Active/primary | 2-3 |
| *gardenia jasminoides* | Active/primary | 1.5-2.5 |
| *Gentiana scabra* | Active/primary | 2-3 |
| *Scutellaria baicalensis* | Active/primary | 2-3 |

TABLE 2-continued

| AHN | Type | % per 750 mg Tablet |
|---|---|---|
| *Zingiber officinale* | Active/secondary | 0-2 |
| *Angelica polymorpha* | Active/secondary | 0-2 |
| *Glycyrrhiza uralensis* | Active/secondary | 0-1.5 |
| Starch-Potato | Excipient | 48-50 |

In order to prepare the tablets, each of the above raw materials are loaded into an extractor and water is added, up to ten times the weight of the combined raw material. The proportions of materials that make up the raw mixture is depicted in Table 3. The mixture is then allowed to soak for an hour before it is brought to boil at 100° C. The mixture is retained at this temperature for approximately one hour after which the liquid is extracted to a dedicated storage tank and the extractor is refilled with water in accordance with the above volume and the extraction process is repeated.

TABLE 3

| AHN | Equivalent Qty (mg) | Raw Prescription (g) | Range of percentage by ratio (%) |
|---|---|---|---|
| *Prunus persica* | 107 | 9 | 3.8-7.6 |
| *Carthamus tinctorius* | 107 | 9 | 3.8-7.6 |
| *Salvia miltiorrhiza* | 107 | 9 | 3.8-5.7 |
| *Oldenlandia diffusa*, Herba | 146 | 12 | 5.7-7.6 |
| *Angelica dahurica* | 146 | 12 | 3.8-7.6 |
| *Gleditsia sinensis*, Spina | 146 | 12 | 3.8-7.6 |
| *Viola yedoensis*, Herba | 146 | 12 | 3.8-7.6 |
| *Taraxacum mongolicum*, Herba | 146 | 12 | 0-7.6 |
| *Lonicera japonica* | 146 | 12 | 0-7.6 |
| *Phellodendron amurense* | 107 | 9 | 2.5-5.7 |
| *Paeonia suffruticosa* | 107 | 9 | 3.8-7.6 |
| *gardenia jasminoides* | 71 | 6 | 3.8-7.6 |
| *Gentiana scabra* | 107 | 9 | 2.5-7.6 |
| *Scutellaria baicalensis* | 107 | 9 | 5.7-7.6 |
| *Zingiber officinale* | 71 | 6 | 0-3.8 |
| *Angelica polymorpha* | 71 | 6 | 0-5.7 |
| *Glycyrrhiza uralensis* | 47 | 4 | 0-3.8 |

The extracted liquid is then fed to a concentrator where the liquid is maintained at 40-60% for two hours until the water content is reduced to around 35-60% and the liquid takes the consistency of a paste. This concentrated paste is then refrigerated.

The carrier, in this embodiment, potato starch is then added into a granulator and the concentrated paste is sprayed into the granulator where the temperature is set at around 55-65° C. Analysis is able to be performed on the granules produced in this process for quality control purposes, after which the granules are mixed with a further excipient, such as magnesium stearate then to forming the tablets. The tablets are then packaged in bottles for distribution.

The composition of the ingredients of the present disclosure is determined based on the knowledge that acne is largely caused by heat, blood stagnation, toxicity and inflammation in the skin. The above referenced primary ingredients have been selected to address each of these issues to reduce inflammation and increase circulation and blood flow and maintaining a health skin temperature that avoids toxin build-up.

The tablets of the present disclosure may be recommended to a patient only after an initial consultation with a specialist. In some instances, it may be required that the percentage of the ingredients be increased to address specific issues identified during the consultation process. However, it is also envisaged that the tablets may be provided in retail outlets and the like for purchase without initial consultation.

Throughout the specification and claims the word "comprise" and its derivatives are intended to have an inclusive rather than exclusive meaning unless the contrary is expressly stated or the context requires otherwise. That is, the word "comprise" and its derivatives will be taken to indicate the inclusion of not only the listed components, steps or features that it directly references, but also other components, steps or features not specifically listed, unless the contrary is expressly stated or the context requires otherwise.

It will be appreciated by those skilled in the art that many modifications and variations may be made to the methods of the disclosure described herein without departing from the spirit and scope of the disclosure.

The invention claimed is:

1. A clear skin supplement/medicinal component for acne comprising: an orally administered dosage comprising of between about 3000-9000 mg of a Chinese medicinal composition, comprising by ratio:
   around 3.8-7.6% of each of *Prunus persica, Carthamus tinctorius, Angelica dahurica, Gleditsia sinensis, Viola yedoensis, Paeonia sujfruticosa*, and *Gardenia jasminoides;*
   around 5.7-7.6% of each of *Oldenlandia diffusa* and *Scutellaria baicalensis;*
   around 3.8-5.7% of *Salvia miltiorrhiza;*
   around 2.5 5.7% of *Phellodendron amurense;*
   around 2.5-7.6% of *Gentiana scabra;* and
   around 0-7.6% of each of *Taraxacum mongolicum* and any one of *Lonicera japonica, Rhizoma coptidas*, and *Sophora flavescens.*

2. The supplement according to claim 1, wherein the Chinese medicinal composition also comprises by ratio between 0-3.8% of each of *Zingiber officinale* and *Glycyrrhiza uralensis*; and 0-5.7% of *Angelica polymorpha*.

3. A method of administering a supplement in accordance with claim 1, wherein the supplement is provided in tablet form and the tablet is ingested by the user.

4. A method or forming a clear skin supplement/medicinal component for treating acne comprising method or forming a supplement in accordance with claim 1, comprising:
   loading the raw materials into an extractor;
   adding water to the extractor, up to ten times the weight of the combined raw materials;
   mixing the mixture of raw materials and water within the extractor; soaking the mixture for a predetermined period of time; boiling the mixture at around 100° C. and retaining the mixture at around 100° C. temperature for approximately one hour;
   extracting the remaining liquid into a dedicated storage tank;
   refilling the extractor with water up to ten times the weight of the combined raw materials and repeating the mixing, soaking, boiling and extracting steps;
   feeding the extracted liquid to a concentrator where the liquid is maintained at 40-60° C. for approximately two hours until the water content is reduced to around 35-60% and the liquid has a consistency of a paste;
   removing the paste from the concentrator refrigerating the paste; adding a carrier into a granulator;
   spraying the granulator with the concentrated paste at a temperature of around 55-65° C. to form granules; and
   mixing the granules with a further excipient to form tablets.

* * * * *